(12) United States Patent
Mader

(10) Patent No.: US 8,720,715 B2
(45) Date of Patent: May 13, 2014

(54) CLOSURE CAP FOR A MEDICINE CONTAINER

(75) Inventor: Jürgen Mader, Dambach (DE)

(73) Assignee: Spang & Brands GmbH, Friedrichsdorf (DE)

( * ) Notice: Subject to any disclaimer, the term of this patent is extended or adjusted under 35 U.S.C. 154(b) by 528 days.

(21) Appl. No.: 12/867,633

(22) PCT Filed: Jan. 21, 2009

(86) PCT No.: PCT/EP2009/000340
§ 371 (c)(1),
(2), (4) Date: Aug. 13, 2010

(87) PCT Pub. No.: WO2009/100806
PCT Pub. Date: Aug. 20, 2009

(65) Prior Publication Data
US 2010/0326990 A1    Dec. 30, 2010

(30) Foreign Application Priority Data

Feb. 15, 2008   (DE) .......................... 10 2008 009 418

(51) Int. Cl.
*B65D 41/00*   (2006.01)
(52) U.S. Cl.
USPC .......................... 215/247; 604/415; 222/541.1
(58) Field of Classification Search
USPC .......................... 215/247, 249, 253; 604/415; 222/153.07, 541.1, 541.6
See application file for complete search history.

(56) References Cited

U.S. PATENT DOCUMENTS

| 3,888,377 | A * | 6/1975 | Stadler | 215/249 |
| 7,137,519 | B2 * | 11/2006 | Becker | 215/249 |
| 7,334,310 | B2 * | 2/2008 | Becker | 29/458 |

FOREIGN PATENT DOCUMENTS

| DE | 3 835 720 | 5/1990 |
| DE | 44 25 433 | 2/1996 |
| DE | 103 11 154 | 9/2004 |

OTHER PUBLICATIONS

International Preliminary Report on Patentability and English translation of the Written Opinion of the International Searching Authority issued Sep. 7, 2010 for International Application No. PCT/EP2009/000340, The International Bureau of WIPO, Geneva, Switzerland.
International Search Report for PCT/EP2009/000340.

* cited by examiner

*Primary Examiner* — J. Gregory Pickett
*Assistant Examiner* — Raven Collins
(74) *Attorney, Agent, or Firm* — Stites & Harbison PLLC; Marvin Petry

(57) ABSTRACT

A closure cap for medicine containers and the like, having a bowl-shaped outer part made of PE or PP having at least one exposable penetration opening and a sealing element made of a soft plastic covering said opening. In order to obtain a reliable tight connection between the outer part and the sealing element, the sealing element is tightly connected all around to a socket encompassing the circumference thereof by injection into the same, and the socket is tightly welded around the entire circumference thereof to the outer part or otherwise tightly connected thereto.

9 Claims, 4 Drawing Sheets

Figure 1:
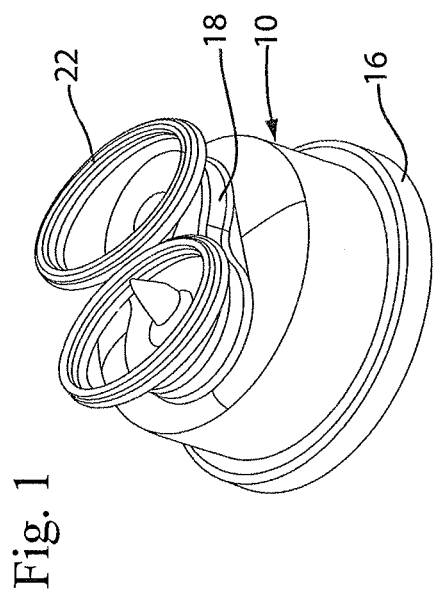

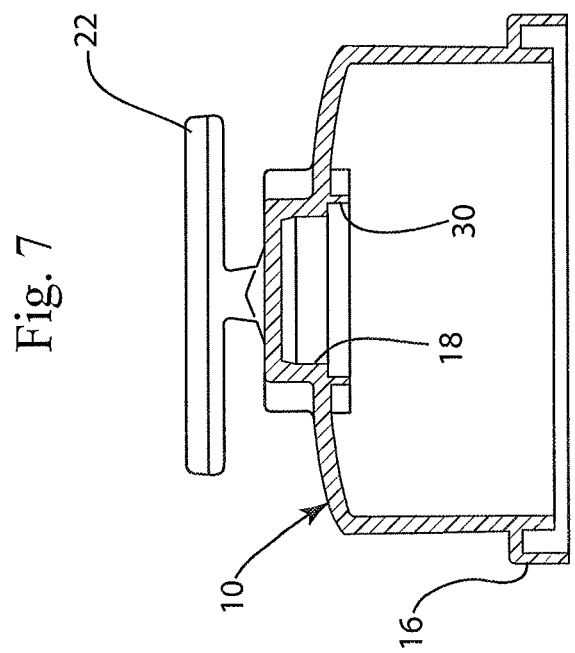
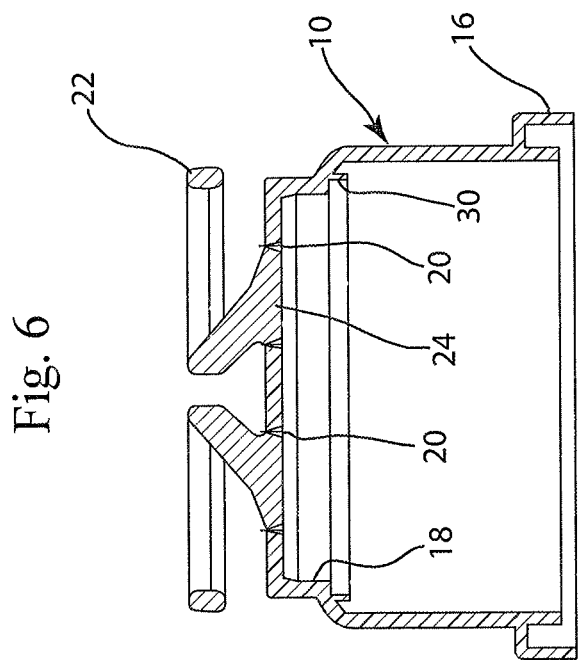

CLOSURE CAP FOR A MEDICINE CONTAINER

The invention relates to a closure cap for tight connection with a container in material-locking fashion (in material-to-material connection), which container contains a fluid pharmaceutical substance, having an essentially cup-shaped outer part of thermoplastic with at least one tightly covered, exposable penetration opening on the face end and with a disk- or stopperlike sealing element of a soft plastic, covering the penetration opening on the inside. The invention further relates to a method for producing such a closure cap, and to a thermoplastic container filled with a fluid pharmaceutical substance.

A closure cap of this kind is known from German Patent DE 3 835 720 C2. It is produced by injecting the material for the sealing element into the outer part of the closure cap in an injection mold, so that after hardening it is solidly joined to the closure cap. However, since the injected material of the sealing element would also be connected solidly to a covering, formed in one piece with the outer part and capable of being torn off, of the penetration opening, the covering must be attached afterward, for instance in the form of a glued-on metal foil, and can comparatively easily be damaged.

Further closure caps of this kind are known from German Patent DE 44 25 433 C1 and German Patent Disclosure DE 103 11 154 A1. In both cases, a sealing element of soft plastic is welded annularly around the penetration opening to the outer part of the cap by means of locally limited heating. However, in the meantime it has been found that it is quite difficult in large-scale mass production to produce durably reliable, tight welded connections between the soft plastic of the sealing element and the material of the outer part of the closure cap. Again and again, it was found that right after the requisite sterilizing procedure, a welded connection was unpredictably no longer tight. The precise causes for the rupture of the welded connection are not yet known. It is assumed that the difficulties are due primarily to the very different materials comprising the outer part and the sealing element.

It is therefore the object of the invention to create a closure cap of the type defined at the outset and a method for its production as well as a container having a closure cap, in which even in large-scale mass production, a reliably tight connection between the outer part and the sealing element is achieved, regardless of how the outer covering of the penetration opening is designed.

The aforementioned object is attained according to the invention on the one hand in that the sealing element is connected, by injection into a socket surrounding its circumference, tightly all the way around to this socket, and the socket is tightly connected, preferably welded, over its entire circumference to the outer part.

Thus instead of a single connection, the invention now proposes two parallel connections. In a purely theoretical consideration of random flaws, it would have been expected that as a result the likelihood of a flaw of the seal would be doubled overall. In fact, however, a greater degree of safety is attained, because each of the two parallel connections can be produced, reliably tightly beyond the sterilizing procedure, with much greater safety. If as in the known version the outer part of the closure cap comprises PE (polyethylene) or PP (polypropylene) and the sealing element comprises an injection-moldable thermoplastic elastomer (TPE), then to attain a tight welded connection, for the socket PE or PP or a thermoplastic compound material can for instance be used, which as an adhesion promoter contains on the one hand material that is connectable in material-to-material fashion to that of the sealing element and on the other material that is connectable in material-to-material fashion to that of the outer part. Normally, such a compound material is composed of components of both the material of the outer part and of the material of the sealing element.

The socket surrounding the sealing element can be welded on one of its end faces and/or on its circumferential surface to the outer part. In a preferred embodiment of the invention, the cup-shaped outer part is formed with a bowl-shaped indentation in its bottom, which indentation surrounds the penetration opening, and the cross section of the indentation fits the cross section of the socket; and that the socket is formed, on the end toward the container, with a flange which is welded to the outer part. The welded connection can be improved still further by providing that on the periphery of the bowl-shaped indentation, the outer part is formed with a relatively thin-walled collar surrounding the indentation and protruding from the inner bottom face, which collar is welded to the flange that is integrally formed onto the socket. Moreover, this embodiment has the advantage that the collar facilitates the insertion of the socket, with the sealing element contained in it, into the outer part before the welding.

As also known from other closure caps, in the preferred practical embodiment the outer part is formed with two penetration openings and two bowl-shaped indentations surrounding them, which indentations merge with one another, and then the sealing elements for the two penetration openings are likewise formed merging in one piece with one another. In that case, the sealing elements connected in one piece are together surrounded by a single socket. An alternative version provides that the outer part is formed with two penetration openings and one bowl-shaped indentation, in which indentation two separate sealing elements are seated in a common, well-fitting, one-piece socket.

Since according to the invention the material for the sealing element is not injected directly into the outer part of the closure cap but rather into a socket, which is subsequently welded into the outer part or optionally glued in place or clipped in place with a tight seat, the penetration openings can be covered by an end wall region, formed in one piece with the outer part and defined by a rated breaking line, the end wall region having an integrally formed-on grip tab or grip eyelet.

The proposed new method for producing the novel closure cap corresponds to the above-described construction of the novel closure cap. Accordingly, first the outer part and the socket are created as separate parts in the injection-molding process. Next, again in an injection mold, the material of the sealing element is injected into the socket, so that after the curing, the socket surrounds the sealing element that is tightly connected to it. Finally, depending on the shape of the outer part, the socket is welded in a known manner by heating, which can also be produced by laser or connected in some other way to the outer part on the face end or on the circumference.

Finally, the subject of the invention is also a container with a fluid pharmaceutical substance contained in it and with a closure cap according to the invention.

Figure 4:
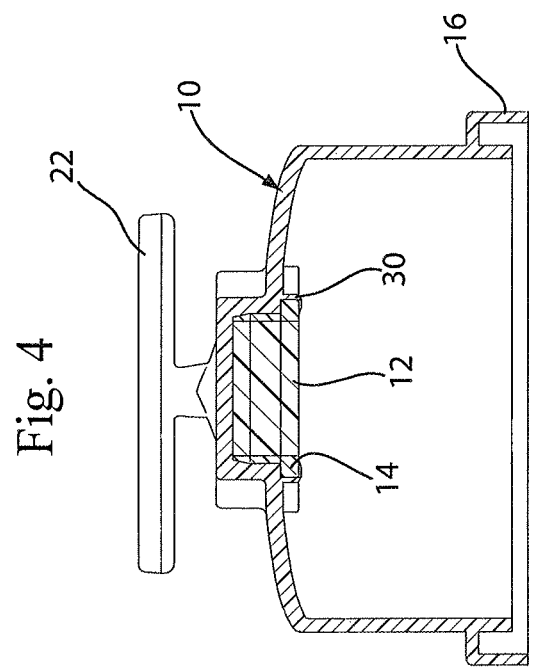
Figure 3:
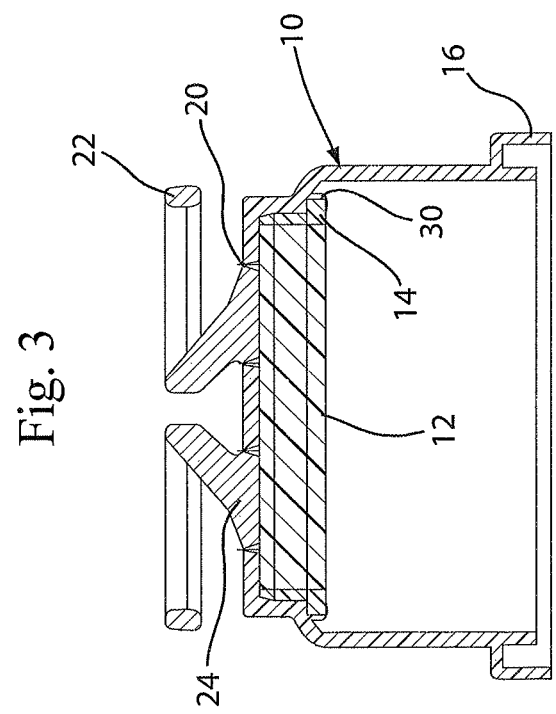
Figure 5:
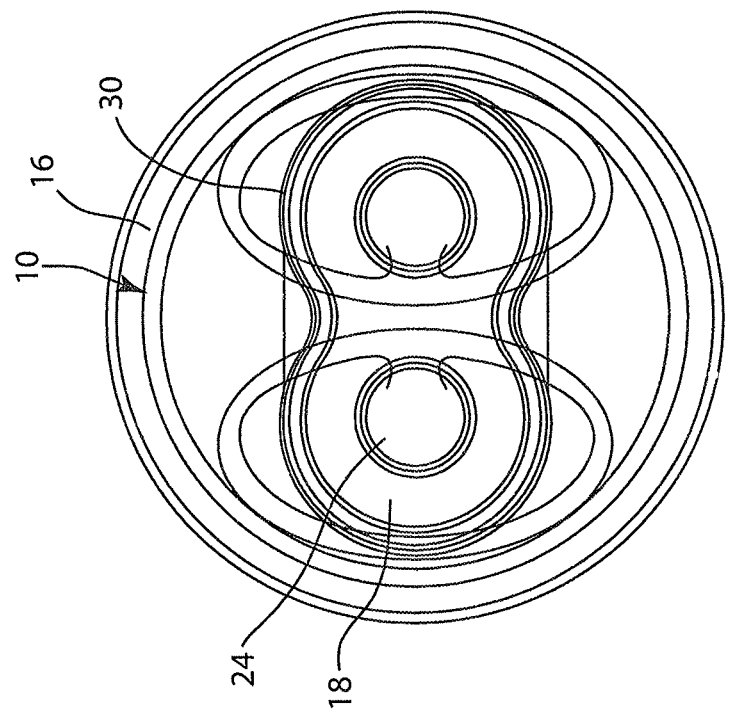
Figure 2:
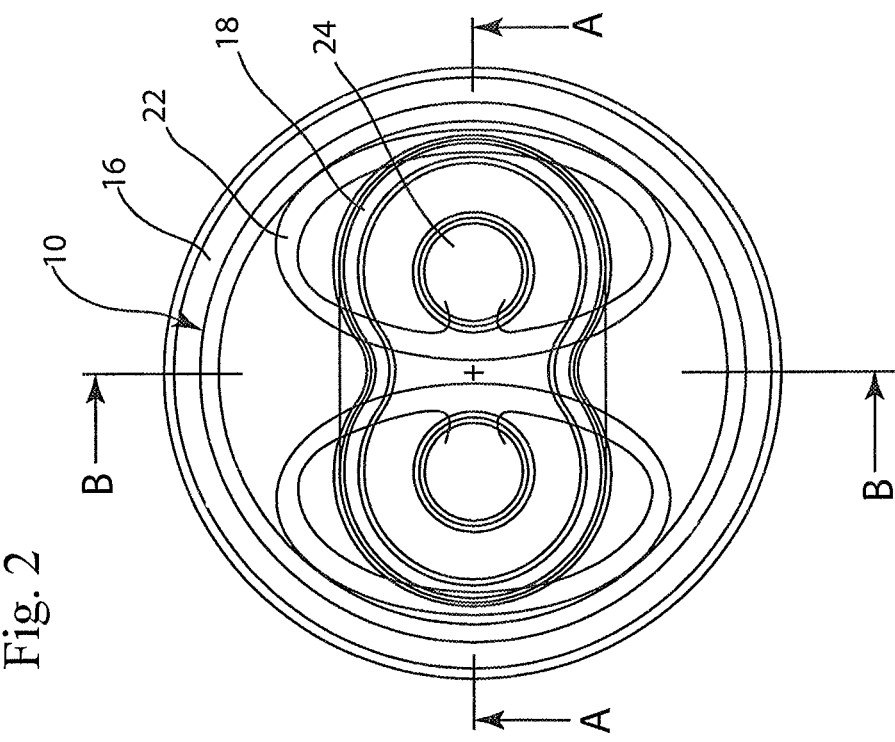
Figure 9:
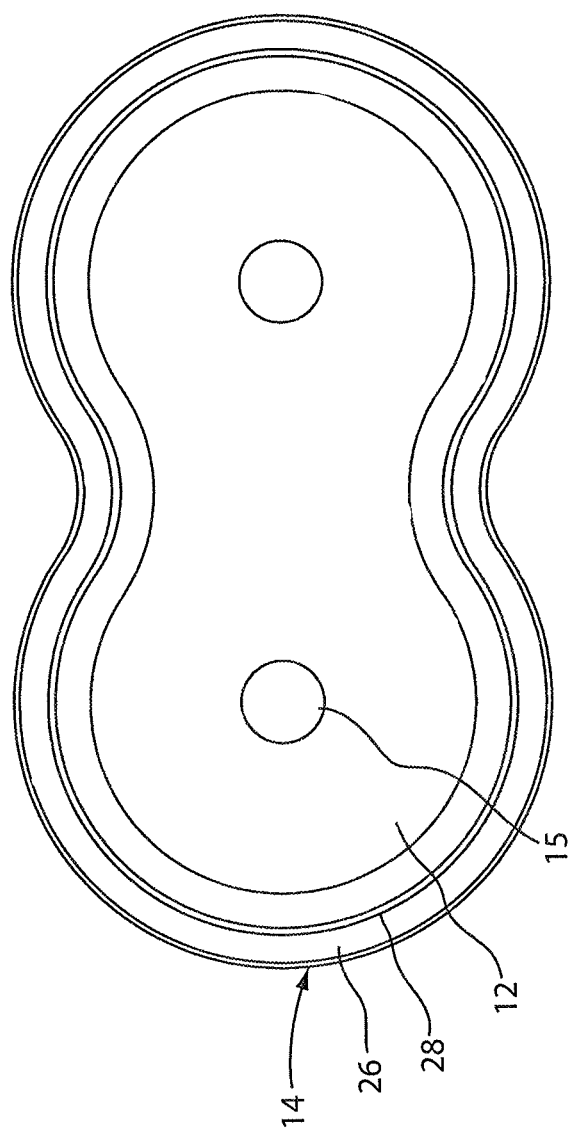
Figure 8:
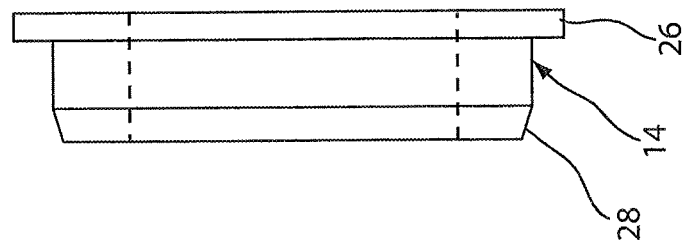
Figure 10:
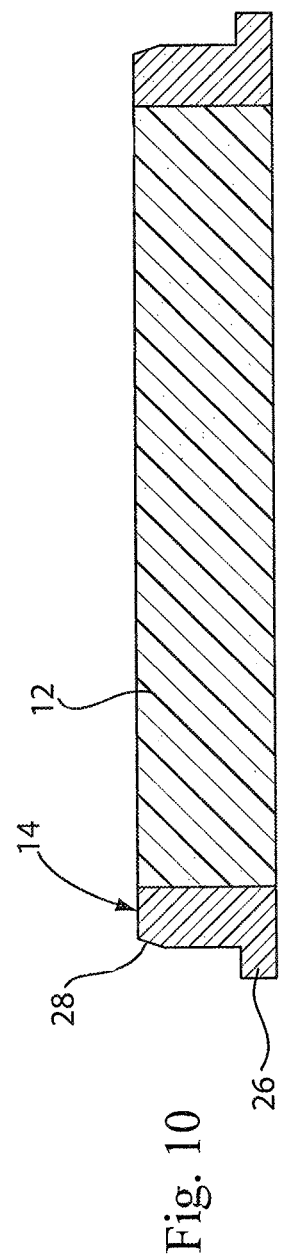

Below, an exemplary embodiment of the invention shown in the accompanying drawings will be described in further detail. The drawings show:

FIG. 1, a perspective view of a closure cap of the invention;
FIG. 2, a top view on the closure cap of FIG. 1;
FIG. 3, a cross section through the closure cap taken along the line A-A in FIG. 2;
FIG. 4, a cross section through the closure cap taken along the line B-B in FIG. 2;

FIG. 5, a view from below on the outer part of the closure cap of FIGS. 1 and 2 before the insertion of the sealing element;

FIG. 6, a cross section of the outer part of the closure cap of FIG. 5, taken along the line A-A in FIG. 2;

FIG. 7, a cross section of the outer part of the closure cap of FIG. 5, taken along the line B-B in FIG. 2;

FIG. 8, a side view of a socket for receiving the sealing element of the closure cap;

FIG. 9, a top view on the socket of FIG. 8 after the injection and hardening of the sealing element; and FIG. 10, a longitudinal section through the socket and the sealing element seated in it with a tight connection.

The closure cap shown in FIGS. 1 through 4 comprises an essentially cup-shaped outer part 10, for instance of polyethylene (PE) or polypropylene (PP); a sealing element 12 comprising a thermoplastic elastomer (TPE); and a socket 14, surrounding the sealing element 12 on its circumference, of PE or PP or a compound material which contains components of both the material of the outer part 10 and of the material of the sealing element 12.

The outer part 10, on its lower, open end, has a flange rim 16, which in a known manner is to be joined all the way around tightly to the suitably embodied neck of a container that contains a pharmaceutical product. A bowl-shaped indentation 18 is formed into the bottom of the cup-shaped outer part 10; it has the elongated form, visible in FIGS. 2 and 5, of two cylindrical indentations merging with each other, with a waist in the middle transitional region. It is understood that the transitional region could also be rectilinearly tangential, or the entire indentation could have an essentially elliptical cross section. The form shown with the waist was selected with a view to minimizing the cross-sectional area. As a result, the mass of the sealing element 12 seated in the bowl-shaped indentation 18 is also reduced.

However, in the closure cap shown, the material comprising the sealing element 12 has not been injected directly into the outer part 10. That would have meant that in the injection-molding process, it would have been joined solidly to the cup-shaped outer part 10 not only on the circumference but also on the face end over the entire bottom face of the outer part. That would have made it impossible for parts of the face-end wall, forming the bottom, that are each bounded by a rated breaking line 20, to be separated by being torn out, as in the closure cap shown, in order to expose penetration openings for cannula-like connection ends of infusion tubing. In the exemplary embodiment, the closure cap has two penetration openings, bounded by rated breaking lines 20, and these openings can be exposed individually by pulling on oval eyelets 22 that are each integrally formed onto a region 24 of the end wall that is bounded by an annularly closed rated breaking line 20.

To prevent the sealing element 12 from sticking firmly to the end wall regions 24 of the outer part 10, it has been produced separately from the outer part 10 and then inserted into the bowl-shaped indentation 18 and secured there.

Because the sealing element 12 of TPE, as already noted at the outset, cannot be reliably welded to the outer part of PP or PE of the closure cap, in the invention it is injected into the socket 14 formed previously by injection molding in an injection mold, and at the inner face of the socket 14, a solid, tight connection to the sealing element 12 is created when, as in European Patent Disclosure EP 0 364 783 B1 the outer part, the socket 14 is of PE or PP and the sealing element 12 is of a TPE. To improve the tight material-to-material connection between the socket 14 and the sealing element 12 still further, the socket 14 can be formed of an injection-moldable compound material, which, like the outer part 10, comprises PE or PP and which additionally, as an adhesion promoter, has components of the material of the sealing element.

Preferably, the socket 14 has the shape shown in FIGS. 8 and 9 of two round rings merging with one another at a waist, and also has the cross section visible in FIG. 10, with an outer flange 26 on one end and a chamfer 28 on the other end. The inner face of the socket 14 is shown as axially rectilinear in FIG. 10, but it can also be shaped for instance with axial or radial ribs or grooves, if that should prove necessary for the sake of a firm hold of the sealing element 12.

In the exemplary embodiment, the sealing element 12 is flush on the face end with the end faces of the socket 14 and as shown in FIG. 9 can be shaped with a depression 15 in the center of each of the penetration openings, which makes it easier to pierce with a cannula. The sealing element 12 could, however, also be formed such that on the side where the chamfer 28 is located, it protrudes slightly past the end face of the socket 14, and in the finished state of the closure cap rests annularly around the rated breaking line 20 with slight prestressing on the bottom of the indentation 18.

As can seen best from FIGS. 6 and 7, the outer part 10 is formed annularly around the bowl-shaped indentation 18 with a relatively thin-walled collar 30 extending axially toward the open end. The spacing of the collar 30 from the outer peripheral edge of the indentation 18 is equivalent to the width of the flange 26 of the socket 14. The outer outlines of the socket 14 with a flange 26 on the one hand, and the indentation 18 and the collar 30 on the other, are selected such that the flange 26 fits into the collar 30, and the remaining axial portion of the socket 14, with the chamfer 28 made on the front end, fits into the suitably shaped indentation 18 that tapers toward the end. The chamfer 28 here has the advantage of easier introduction of the socket 14 into the indentation 18 and of a solid and suitably tight seat in the tapered end of the indentation 18. The collar 30, also, promotes the positioning of the socket 14 upon the assembly of the sealing element 12 and facilitates tight welding of the socket 14 to the outer part 10 of the closure cap by means of a suitably shaped heating element, which quickly heats the thin-walled collar 30 and the likewise relatively thin-walled flange 26 to the requisite welding temperature, so that a tight welded connection comes about annularly around the socket 14.

The heating of a region of the socket 14 and of an adjoining region of the outer part 10 at the location mentioned or some other location of the socket 14 could also be done in some other way, for instance by means of a laser, optionally from the outside through the wall of the outer part if the outer part 10 is transparent or translucent. Welding the socket 14 to the outer part 10 by ultrasonic welding is also possible, if it is ensured by the shaping of the rated breaking lines 20 that they will not become leaky as a result of the oscillations in the ultrasonic welding.

The invention claimed is:

1. A closure cap for tight connection with a container in material-locking fashion, which container contains a medical substance, having an essentially cup-shaped outer part of thermoplastic with at least one tightly covered, exposable penetration opening on a face end and with a sealing element of a soft plastic, covering the penetration opening on the inside of the outer part, wherein the sealing element is connected, by injection into a socket surrounding the circumference of the sealing element, tightly all the way around to this socket, and the socket is tightly connected over the entire circumference of the socket to the outer part, the socket, on one end face of the socket and/or the circumferential surface of the socket being welded to the outer part, the bottom of the cup-shaped out part being formed with a bowl-shaped indentation, which indentation surrounds the penetration opening, and the cross section of the indentation fits the cross section of the socket; and the socket is formed, on the end toward the container, with a flange which is welded to the outer part, and wherein on the periphery of the bowl-shaped indentation, the outer part is formed with a collar surrounding the indentation and protruding from the inner bottom face, which collar is welded to the flange that is integrally formed onto the socket.

2. The closure cap as defined by claim 1, wherein the socket is tightly welded to the outer part.

3. The closure cap as defined by claim 1, wherein the outer part comprises PE (polyethylene) or PP (polypropylene), and the sealing element comprises an injection-moldable thermoplastic elastomer (TPE).

4. The closure cap as defined by claim 2, wherein the socket comprises PE, PP or a thermoplastic compound material, which contains a material that is connectable in material-locking fashion to the material of the sealing element, or a material that is weldable to the material of the outer part.

5. The closure cap as defined by claim 4, wherein the compound material contains components of the material of the outer part and of the sealing element.

6. The closure cap as defined by claim 1, wherein the penetration opening or penetration openings (20, 24) are each covered by an end wall region, formed in one piece with the outer part and defined by a rated breaking line, the end wall region having an integrally formed-on grip tab or grip eyelet.

7. A thermoplastic container filled with a fluid pharmaceutical substance, which is tightly welded into a closure cap as defined by claim 1.

8. A closure cap for tight connection with a container in material-locking fashion, which container contains a medical substance, having an essentially cup-shaped outer part of thermoplastic with at least one tightly covered, exposable penetration opening on a face end and with a sealing element of a soft plastic, covering the penetration opening on the inside of the outer part, wherein the sealing element is connected, by injection into a socket surrounding the circumference of the sealing element, tightly all the way around to this socket, and the socket is tightly connected over the entire circumference of the socket to the outer part, the socket, on one end face of the socket and/or the circumferential surface of the socket being welded to the outer part, the bottom of the cup-shaped out part being formed with a bowl-shaped indentation, which indentation surrounds the penetration opening, and the cross section of the indentation fits the cross section of the socket; and the socket is formed, on the end toward the container, with a flange which is welded to the outer part, and wherein the out part is formed with two penetration openings and two bowl-shaped indentations surrounding them, which indentations merge with one another; and the sealing elements for the two penetration openings are formed merging in one piece with one another and together are surrounded by a single socket.

9. A closure cap for tight connection with a container in material-locking fashion, which container contains a medical substance, having an essentially cup-shaped outer part of thermoplastic with at least one tightly covered, exposable penetration opening on a face end and with a sealing element of a soft plastic, covering the penetration opening on the inside of the outer part, wherein the sealing element is connected, by injection into a socket surrounding the circumference of the sealing element, tightly all the way around to this socket, and the socket is tightly connected over the entire circumference of the socket to the outer part, the socket, on one end face of the socket and/or the circumferential surface of the socket being welded to the outer part, the bottom of the cup-shaped out part being formed with a bowl-shaped indentation, which indentation surrounds the penetration opening, and the cross section of the indentation fits the cross section of the socket; and the socket is formed, on the end toward the container, with a flange which is welded to the outer part, and wherein the outer part is formed with two penetration openings and one bowl-shaped indentation, in which indentation two separate sealing elements are seated in a common, one-piece socket.

* * * * *